United States Patent [19]

Jestrich et al.

[11] Patent Number: 4,577,505
[45] Date of Patent: Mar. 25, 1986

[54] SPECIAL ANGLE BEAM PROBE FOR ULTRASONIC TESTING

[75] Inventors: Hans-Achim Jestrich, Ratingen; Paul Friedrich, Uttenreuth, both of Fed. Rep. of Germany

[73] Assignee: Kraftwerk Union Aktiengesellschaft, Mülheim, Fed. Rep. of Germany

[21] Appl. No.: 634,990

[22] Filed: Jul. 27, 1984

[30] Foreign Application Priority Data

Aug. 1, 1983 [DE] Fed. Rep. of Germany ....... 3327736

[51] Int. Cl.⁴ ............................................. G01N 29/04
[52] U.S. Cl. ......................................... 73/629; 73/632; 73/644; 310/336
[58] Field of Search ................. 73/629, 627, 632, 633, 73/642, 644; 310/334, 335, 336

[56] References Cited

U.S. PATENT DOCUMENTS 4,475,054 10/1984 Baumoel .............................. 73/642

FOREIGN PATENT DOCUMENTS 451943 4/1975 U.S.S.R. ................................ 73/633

Primary Examiner—Stephen A. Kreitman
Attorney, Agent, or Firm—Herbert L. Lerner; Laurence A. Greenberg

[57] ABSTRACT

A special angle beam probe for ultrasonic testing includes at least one ultrasonic vibrator fastened in a beam probe housing on a wedge-shaped support body which may be formed of Plexiglass, using damping means. The ultrasonic beam of the vibrator strikes the surface of the test piece at an incidence angle other than 0°, as measured from a perpendicular at the surface of the test piece at the point where the beam strikes. The ultrasonic beam furthermore strikes the test piece surface at an oblique angle between 0° and 360° subtended between a principal beam probe axis and the beam, as seen in the direction perpendicular to the beam probe from above. The novelty of the invention is that the special angle beam probe includes a multiplicity of prefabricated beam probe subassemblies. The ultrasonic vibrator of each subassembly is fastened with a predetermined incidence angle within a first beam probe housing. A second beam probe housing contains the test head subassembly and the test head subassembly can be fastened at least at one predetermined oblique angle within the second housing for forming the overall special angle beam probe. In this way a multiplicity of beam probe subassemblies with the same insonification angle form special angle beam probes with different, predetermined oblique angles, by assembling the subassemblies in second test head housings in different oblique angle relationships.

25 Claims, 16 Drawing Figures

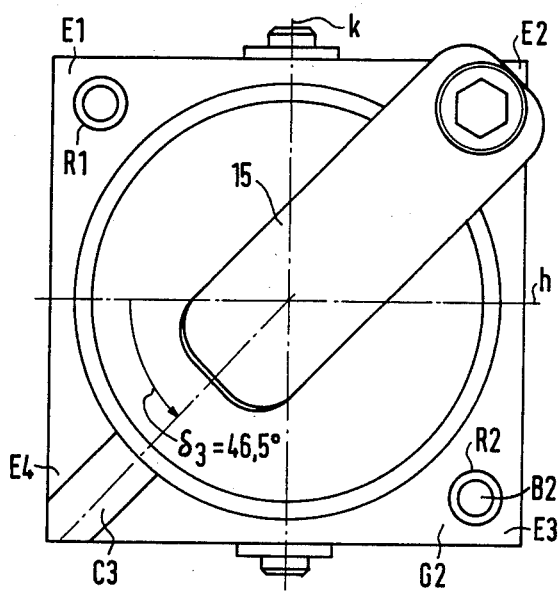
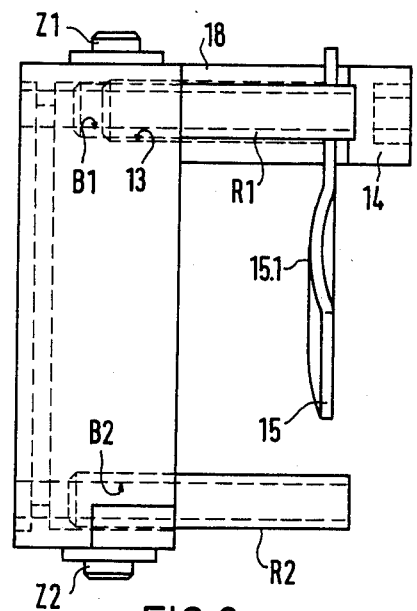
FIG 8  FIG 9
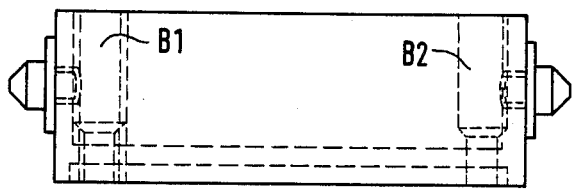
FIG 11
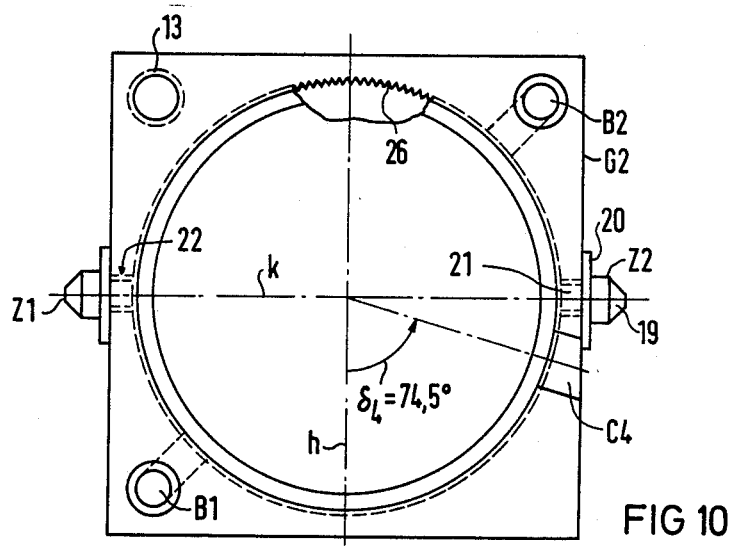
FIG 10

SPECIAL ANGLE BEAM PROBE FOR ULTRASONIC TESTING

CROSS REFERENCE TO RELATED APPLICATION

The invention is related to co-pending Application Ser. No. 613,902, filed May 24, 1984 and owned by the assignee of the instant application.

BACKGROUND OF THE INVENTION

1. Field of the Invention

The invention relates to a special angle beam probe for ultrasonic testing with at least one ultrasonic vibrator disposed and fastened in a beam probe housing on a wedge-shaped support body which is formed, in particular, of Plexiglass, and damping means, the ultrasonic beam of the ultrasonic vibrator striking the surface of the test piece at an incidence angle $\alpha \neq 0$ relative to the perpendicular or normal of the beam probe, at a point along the surface of the test piece where the beam strikes, the ultrasonic beam further striking the surface of the test piece, and the ultrasonic beam arriving at the surface of the test piece at an oblique angle $\delta$ subtended between a principal or beam probe reference axis and the U.S. beam, wherein $0 \leq \delta \leq 360°$, as seen in a plan view along the direction perpendicular to the beam probe.

2. Description of the Prior Art:

Such an angle beam probe is known, for instance, from the book "Zerstoerungsfreie Werkstoffpruefung" (non-destructive material testing) by Pál Réti, S. Hirzel Publishers, Stuttgart, Germany, page 196, FIG. 203.

The main areas of application of such angle beam probes are general material testing with ultrasound and in particular the testing of welded seams. Due to the ultrasonic ray incident at an angle with respect to the perpendicular under the incidence angle $\alpha$, it is possible to detect and evaluate material separations of a given area, which are located perpendicular to or at an angle with respect to the surface, such as cracks and bonding defects. A further area of application of ultrasonic testing with angle beam probes is the testing of disc bodies shrunk-on to shafts in vicinity of shrink fittings and the adjoining regions, especially in vicinity of internal hub surfaces and axial anti-rotation devices in rotor discs of low-pressure turbine rotors. In such cases the rotor discs, as seen in cross section, have lateral faces tapered in the radial direction from the inside out approximately in the shape of a club, up to the rim of the wheel.

As is explained in detail in above-mentioned co-pending U.S. application Ser. No. 613,902 filed May 24, 1984, the geometry of such rotor discs is extremely complicated for ultrasonic testing of the non-accessible inner hub surfaces and axial anti-rotation devices with ultrasonic beam probes. Only the lateral faces of the rotor discs are available as coupling areas for the ultrasonic beam probes. In order to carry out such testing operations, special angle beam probes are required which have a certain incidence angle $\alpha$ and a certain oblique angle $\delta$, depending on the wheel disc geometry. The principle of corner reflection of transversal waves is used in this case in the angle-of-impact area of total reflection. This is the so-called corner reflection method, in which the ultrasonic beams are aligned with the test areas of the inner hub surface, and receiving signals are obtained only in the case of flaws. The method of grazing incidence can also be used for checking axial anti-rotation devices.

In order to carry out these testing operations, a multiplicity of special angle beam probes with different pairings of the incidence angle and the oblique angle are required.

It is accordingly an object of the invention to provide special angle beam probe for ultrasonic testing, which overcomes the hereinafore-mentioned disadvantages of the heretofore-known devices of this general type, and to generally reduce the number of special angle beam probes required for solving the test problem, so as to thereby simplify stock-keeping and lower the overall testing costs. It is, in particular, an object of the invention to construct a special angle beam probe of this type in such a manner that the manufacture thereof is substantially simplified and less costly as compared to conventional special angle beam probes which are made individually or in a special production run. A purpose of the invention is to produce special angle beam probes with any desired or unusual oblique angles by a relatively small number of basic angle beam probe types with given incidence angles $\alpha$.

With the foregoing and other objects in view there is provided, in accordance with the invention, a special angle beam probe for ultrasonic testing of a test piece, comprising a multiplicity of prefabricated beam probe subassemblies disposed on a surface of the test piece, the beam probe subassemblies each having a first housing, a wedge-shaped support body disposed in the first housing, at least one ultrasonic vibrator fastened to the support body, and damping means disposed in the first housing, and a multiplicity of second beam probe housings each surrounding a respective one of the beam probe subassemblies, the vibrators each delivering an ultrasonic beam striking a given point along the surface of the test piece at the same predetermined incidence angle other than 0° as measured from a perpendicular or line normal to the surface of the test piece at the given point, the beams arriving at the surface of the test piece at oblique angles between 0° and 360° subtended between a principal or beam probe reference axis of the beam probe and the beam, as seen in direction perpendicular to the beam probe from above, the beam probe subassemblies each being fastenable at least at one different predetermined oblique angle in the second beam probe housings, and the second beam probe housings with the beam probe subassemblies having the same incidence angle and different oblique angles being assembled with different oblique angle relationships.

In accordance with an additional feature of the invention, the first beam probe housings have a cylindrical base body having an opening formed in the bottom thereof and having annular shoulder surfaces at the front thereof, the support bodies have coupling surfaces protruding through the openings in the base bodies, and the second beam probe housings have cylindrical guiding surfaces, bottom sliding surfaces and mounting surfaces spaced from the bottom sliding surfaces in axial direction of the beam probe, the cylindrical base bodies of the beam probe subassemblies having the outer periphery thereof inserted and locked in the cylindrical guiding surfaces of the second beam probe housings, setting the predetermined oblique angle by rotation thereof, the annular shoulder surfaces being in engagement with the mounting surfaces defining annular gaps at the bottom of the beam probe for coupling liquid.

In accordance with another feature of the invention, the second beam probe housings are substantially prismatic rectangular bodies each having a central opening formed therein defining the guiding and mounting surfaces, and the second beam probe housings have corner regions having at least two holes formed therethrough and upwardly-protruding pipe stubs or nozzles integral therewith for connecting coupling liquid feedlines.

In accordance with a further feature of the invention, the second beam probe housings are square, as seen from above.

In accordance with an additional feature of the invention, the pipe stubs are diagonally opposite each other.

In accordance with still another feature of the invention, the annular shoulder surface of the cylindrical base bodies are formed on an annular shoulder, the coupling surfaces of the support bodies are formed on bases thereof, the mounting surfaces of the second beam probe housings are formed on a circular inner shoulder or ring collar and are disposed at a given axial distance from the bottom sliding surfaces and the surface of the test piece, and the sum of the height of the annular shoulder and the thickness of the support body base protruding from the base body for each beam probe subassembly is substantially equal to the given axial distance, whereby the bottom sliding surfaces and coupling surfaces are flush.

In accordance with still a further feature of the invention, there is provided a lid liquid-tightly enclosing and shielding the top of the base body.

In accordance with still an additional feature of the invention, there is provided at least one hold-down spring and a clamping screw anchored in a blind tapped hole formed in vicinity of a corner of the second beam probe housing which is free of the holes, the clamping screw tensioning the hold-down spring against the top or the lid of the beam probe subassemblies in each of the second beam probe housings, pushing the beam probe subassemblies against the mounting surfaces.

In accordance with again another feature of the invention, the clamping screw of each of the second beam probe housings has a shank, and the spring is a forwardly curved leaf spring having a hole formed therein through which the shank passes and a free end, the free end having a spherical part centrally disposed on the top or the lid of the beam probe subassembly.

In accordance with again a further feature of the invention, the second beam probe housings only surround part of the height of the beam probe subassemblies, defining protruding free shell regions of the base body, and including at least one connector jack connected to the vibrators and fastened to the free shell regions.

In accordance with again an additional feature of the invention, the at least one connector jack is in the form of at least two parallel-connected connector jacks fastened to two different points of the periphery of each of the base bodies, whereby one of the jacks is always accessible if the other is covered up due to the squint angle.

In accordance with yet another feature of the invention, the axes of the jacks are radially oriented and form a sector angle of substantially 120°.

In accordance with yet an additional feature of the invention, the coupling surfaces of the support bodies are formed on bases thereof, and including a first marking on the periphery of each of the bases defining a beam probe reference axis where the oblique angle=0°, and the base bodies having a lower peripheral region having a second corresponding counter marking coinciding with the first marking in assembled condition of the beam probe subassemblies.

In accordance with yet a further feature of the invention, the bases of the support bodies are circular discs and the markings are notches.

In accordance with again another feature of the invention, at the point along the periphery of the base bodies having the second markings, the base bodies have radially-oriented posts and the second beam probe housings have radially-extended cuts formed therein receiving the parts, the cuts extending from a point on the guiding surfaces corresponding to the desired squint angle and the cut being exactly matched to the dimensions of the posts for fixing the squint angle without play.

In accordance with again a further feature of the invention, there are provided bearing posts for a gimbal support of a beam probe mounting disposed along another principal axis of the beam probe housing crossing the first-mentioned principal beam probe axis at a right angle on two opposite side walls of the second beam probe housing.

In accordance with still an additional feature of the invention there is provided a spacer bushing mounted on the shank above the top or the lid of the base body.

In accordance with still another feature of the invention, the base body has a gear pitch formed on the outer periphery thereof and the second beam probe housing has a counter gear pitch at the guiding surfaces matching the gear pitch, for changing and securing the oblique angle in accordance with the tooth pitch by rotating the beam probe subassembly relative to the second beam probe housing in angular steps, such as 5°.

In accordance with still a further feature of the invention, the second beam probe housing has substantially radial connecting canals formed therein connecting the holes to the annular gap.

In accordance with again an additional feature of the invention, the support body is formed of a material from the group consisting of resinous and plastic material.

In accordance with a concomitant feature of the invention, there is provided a special angle beam probe for ultrasonic testing of a test piece including a prefabricated beam probe subassembly disposed on a surface of the test piece, the beam probe subassembly having a first housing, a wedge-shaped support body disposed in the first housing, at least one ultrasonic vibrator fastened to the support body, and damping means disposed in the first housing, and a second beam probe housing surrounding the beam probe subassembly, the vibrator delivering an ultrasonic beam striking a given point along the surface of the test piece at a predetermined incidence angle other than 0° as measured from a perpendicular to the surface of the test piece at the given point, the beam arriving at the surface of the test piece at an oblique angle between 0° and 360° subtended between a principal axis of the beam probe and said beam, as seen in direction perpendical to the beam probe from above, the beam probe subassembly being fastenable at least at one predetermined oblique angle in the second beam probe housing.

SUMMARY OF THE INVENTION

The advantages attainable with the invention are in particular that groups of prefabricated beam probe subarrangements or subassemblies can be kept in readiness with given incidence angles α that are used in the test, and are given their final oblique angle δ during their installation and their association with second beam probe housings that are also prefabricated. A cylindrical basic form of the beam probe subarrangement is particularly advantageous from a fabrication and installation point of view. This is because screw machine parts can be made simply and accurately and the adjustment of the oblique angle is permitted by rotating the subarrangement in the second beam probe housing, where the set oblique angle can be fixed by suitable clamping devices. It may be advantageous to attach a scale on the underside of the special angle beam probe at one of the two parts of the beam probe subarrangement which are rotatably adjustable relative to each other on the one hand, and relative to a second beam probe housing on the other hand. A pointer is used in such a manner that the set squint angle can be read directly in degrees. The pointer can also be in the form of a vernier scale so that tenths of degrees can also be set if it is assumed that the vernier is faced by a degree division over part of the periphery of interest, for instance 90°, or over the entire circumference of 360°. This can be advantageously provided especially for angle beam probes with larger dimensions; in the case of smaller dimensions of the special angle beam probe, which is understood to mean a base area of, for instance, 40×40 mm, the setting of the oblique angle is already carried out in the assembly of the finished special angle beam probe in the factory. This is done substantially more accurately with precision gages, to an accuracy of ±0.1 mm which corresponds to an oblique angle tolerance of about ±0.3° for this beam probe size.

Other features which are considered as characteristic for the invention are set forth in the appended claims.

Although the invention is illustrated and described herein as embodied in a special angle beam probe for ultrasonic testing, it is nevertheless not intended to be limited to the details shown, since various modifications and structural changes may be made therein without departing from the spirit of the invention and within the scope and range of equivalents of the claims.

BRIEF DESCRIPTION OF THE DRAWINGS

The construction and method of operation of the invention, however, together with additional objects and advantages thereof will be best understood from the following description of specific embodiments when read in connection with the accompanying drawings, in which:

FIGS. 8 and 9 are respective top and side-elevational views of a second beam probe housing which is modified as compared to FIG. 3, and in which the diagonals for the water connections and a tensioning screw with a lead spring are interchanged, and the oblique angle δ has a different orientation and size;

FIGS. 10 and 11 are respective top and side-elevational views of a second beam probe housing according to FIGS. 8 and 9, however omitting the clamping screw, the lead spring and the water connection, and having an oblique angle which is 74.5° instead of 46.5°, the view of FIG. 10 being rotated counter-clockwise as compared to that of FIG. 8;

DESCRIPTION OF THE PREFERRED EMBODIMENTS

Figure 1:
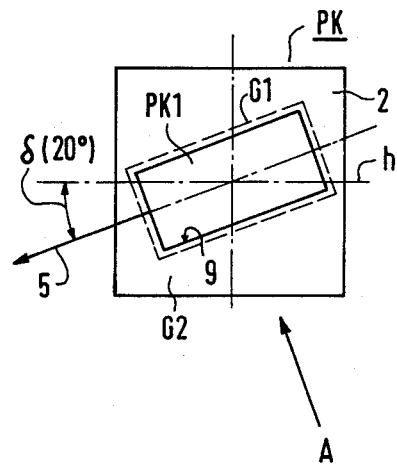
FIG. 1 is a diagrammatic top view of a special angle beam probe, wherein the subarrangement or subassembly of an inner "small" beam probe is inserted into another outer beam probe housing, rotated by an oblique angle δ.
Figure 2:
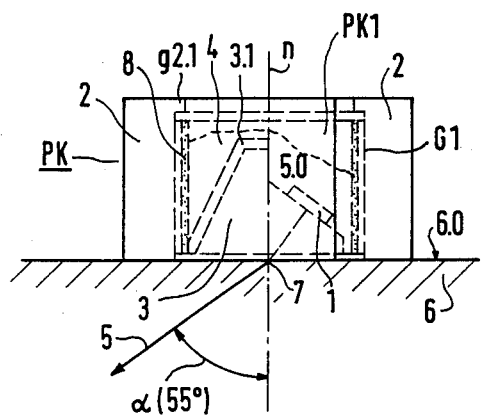
FIG. 2 is a view as seen along the arrow A in FIG. 1, from which the incidence angle can be seen.

Referring now to the figures of the drawings in detail and first, particularly, to FIGS. 1 and 2 thereof, which diagrammatically show the basic principle of the invention, there is seen an ultrasonic vibrator 1 in the form of a piezoelectric ultrasonic transducer disposed and fastened within a beam probe housing 2 on a wedge-shaped support body 3 which is formed, in particular, of Plexiglass. "Plexiglas" is a registered trademark of Rohm and Haas Company, for resinous or plastic material. A damping medium 4 is used in such a manner that an ultrasonic ray 5 of the ultrasonic vibrator 1 arrives at the surface 6.0 of a test piece 6 at an incidence angle α different from 0 and in the case shown, α=55°. The test piece 6 is a steel body, such as the rotor disc of a turbine rotor which is shrunk-onto the shaft of the turbine rotor. The shrink fit must be examined for cracks or flaws. The incidence angle is referred to the perpendicular n taken on the surface of the test piece at the point of impact of the ray, also to be referred to as the normal to the beam probe. The ultrasonic ray 5 is a transversal wave, also known as a shear wave, which is generated at a point of refraction 7, that is also the point of impact if the ultrasonic starting ray 5.0 of the ultrasonic vibrator 1 passes from the relatively thinner medium of the Plexiglass wedge 3 into the relatively denser medium of the steel test piece 6 and is thus refracted away from the perpendicular n. In the drawing, no effort has been made to provide a faithful reproduction of the refraction angles; a diagrammatic example has merely been set forth for purposes of explanation. Since the ultrasonic ray 5 enters the test piece 6 with an incidence angle greater than 0, an angle beam probe is involved. A special angle beam probe is also involved since the ultrasonic ray also meets the surface of the test piece 6.0 at an oblique angle δ. In the plan view as seen the direction of the perpendicular n on the beam probe PK, the oblique angle δ is defined as the angle which is subtended between a principal beam probe axis h, which can also be referred to as the beam probe reference axis, and the ultrasonic ray 5. In principle, δ can be in the range between 0° and 360°. In the case shown, δ=20°. The abbreviation ULS vibrator has been and will continue to be used throughout for the designation of the ultrasonic vibrator; the vibrator can be formed of lead zirconate, barium titanate or quartz, to mention only a few piezocrystalline materials. The support body 3 is preferably formed of Plexiglass or acrylic glass. The wedge shape of the body 3 determines the incidence angle. The shape of the body 3 represents a lead distance for the ULS ray which is originally a longitudinal wave, and is also referred to as a long or pressure wave, wherein the transversal wave for the ULS wave 5 is generated due to the refraction in the region 7. The support body 3 and the damping mass 4 are surrounded by a cork shell 8 which likewise serves for damping. Grooves 3.1 with a zig-zag cross section at the inclined and cover surface of the support body 3, serve for scattering undesirable ULS rays.

In accordance with the invention, the special angle beam probe PK is formed of a beam probe subarrangement PK 1, which forms a prefabricated unit, and has the ULS vibrator 1 which is fastened at a predetermined incidence angle within an associated first beam probe housing G 1. The special angle beam probe PK referred to merely as the "beam probe" below for simplicity also includes a second beam probe housing G 2 which contains the beam probe arrangement PK 1. The beam probe subarrangement or subassembly PK 1 is fastened at a predetermined oblique angle δ in the beam probe housing G 2 and specifically at least one such oblique angle for forming the overall arrangement of the beam probe PK. In this manner, the overall beam probes PK with different predetermined oblique angles δ can be produced from a multiplicity of beam probe subarrangements PK 1 having respective equal incidence angles α, by assembling them with the second beam probe housings G 2 in a different oblique angle relationship. A multiplicity of second beam probe housings G2 are provided, each surrounding a respective one of the beam probe subassemblies PK1. The particular second housing G2 being used is selected for providing a particular oblique angle δ of the subassembly. In the first embodiment according to FIGS. 1 and 2, the beam probe subarrangement PK 1 is rectangular or in the form of a slab, as seen in a plan view, and accordingly a corresponding prismatic recess 9 with a rectangular shape as seen in the plan view, is provided in the second beam probe housing G 2 for receiving the slab. On the cover side of the second beam probe housing G 2, a collar g 2.1 extends over the recess 9 and forms a stop or seating surface when the subarrangement PK 1 is inserted from the bottom. The subarrangement PK 1 is then secured in its assembled position, such as by non-illustrated transversely-oriented clamping screws, which pass through the second housing G 2.

Figure 5:
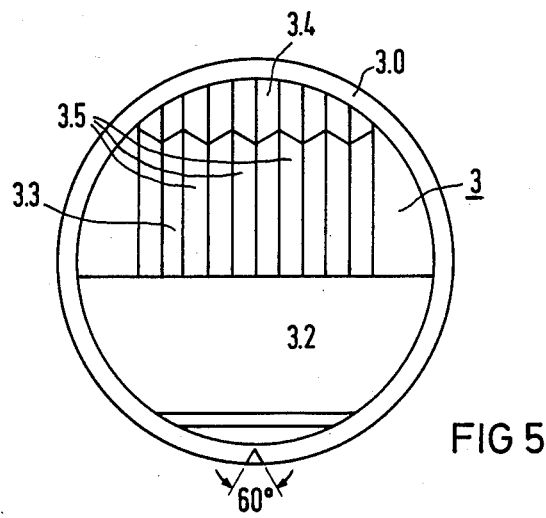
FIG. 5 is a top view of a wedge-shaped support body formed of Plexiglass, for the ultrasonic vibrator according to FIG. 4.
Figure 3:
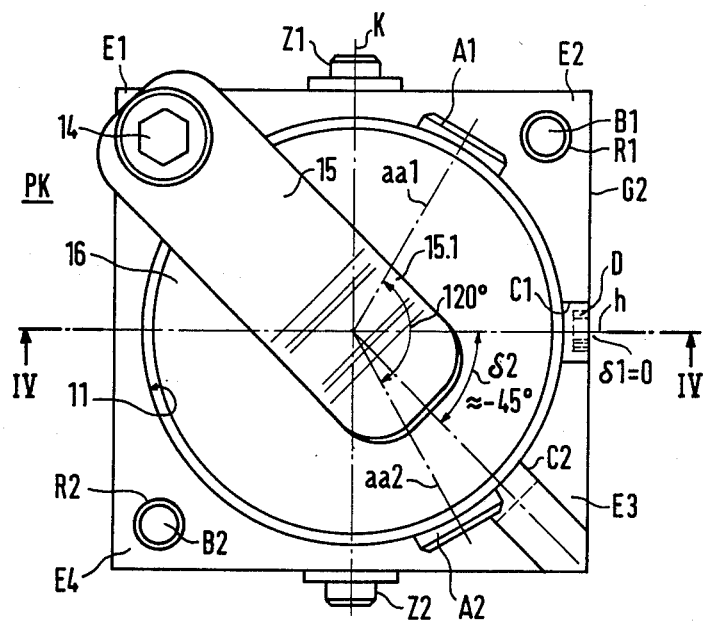
FIG. 3 is a top view of a second embodiment of a special angle beam probe with a cup-like beam probe arrangement, inserted into corresponding guiding and mounting surfaces at the inner periphery of the second beam probe housing.
Figure 6:
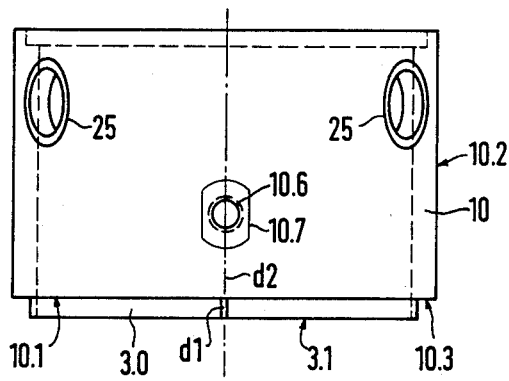
FIG. 6 is a side-elevational view of a cylindrical base body of the cup-shaped subarrangement according to FIGS. 3 and 4.
Figure 7:
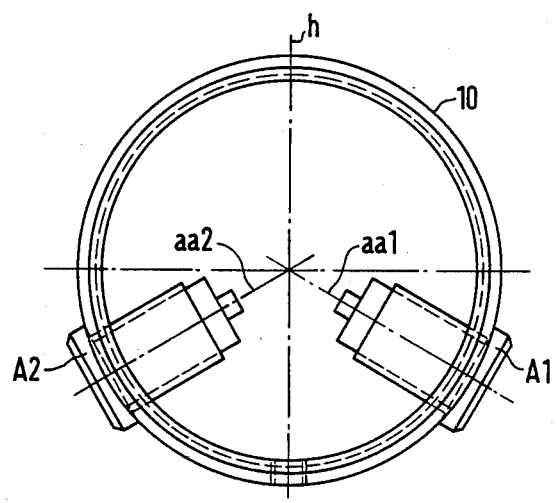
FIG. 7 is a top view of the device shown in FIG. 6, wherein two screwed-in connector jacks are additionally shown.

In the second embodiment according to FIGS. 3 to 7, the first beam probe housing G 1 has a cylindrical base body 10 which is open at the bottom (as best seen in FIGS. 6 and 7). The base body 10 has a bottom opening 10.1 formed therein, through which the support body 3 protrudes with a coupling surface 3.1. The coupling surface 3.1 is the lower surface of a bottom flange 3.0 of the support body 3. The second beam probe housing G 2 has cylindrical guiding surfaces 11.1 corresponding to the outer periphery of the cylindrical base body 10, bottom sliding surfaces 11.2, as well as mounting surfaces 11.3 spaced therefrom axially with respect to the beam probe (in direction along the perpendicular n). The beam probe subarrangement PK 1 is inserted with the cylindrical outer periphery 10.2 of the base body 10 in the guiding surfaces 11.1 at the inner periphery of the second beam probe housing G 2, setting the predetermined oblique angle rotation relationship as shown. The beam probe subassembly PK 1 is also brought into engagement with ring shoulder surfaces 10.3 on the front, with the seating or mounting surfaces 11.3 forming an annular gap 12 on the bottom for coupling liquid and it is locked in this inserted position. In FIG. 3, two oblique angles are shown. The oblique angle δ1=0 (the legs of the angle coincident with the reference axis h) was chosen only because of the sectional presentation in FIG. 4; actually, the oblique angle δ1=0 is only a special case and oblique angles larger than 0, for instance δ2=45°, are used. The minus sign was chosen for oblique angles which are subtended clockwise relative to the reference axis h, whereas the positive angles carrying no sign are subtended counterclockwise.

Figure 4:
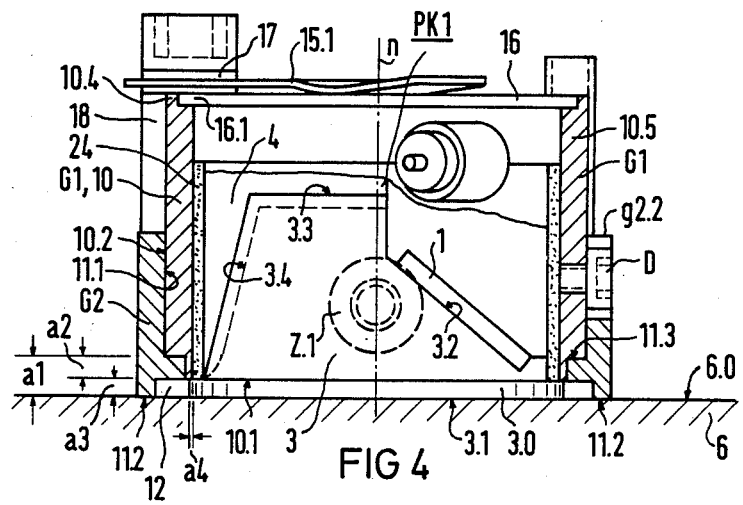
FIG. 4 is a cross-sectional view taken along the line IV—IV in FIG. 3, in the direction of the arrows.

In FIGS. 3 to 7, parts which are the same or analogous to parts in FIGS. 1 and 2 are provided with the same reference symbols; thus, the wedge-shaped support body 3, the damping mass 4, the ULS vibrator 1, etc. are seen in this embodiment. The wedge-shaped support body 3 is once more shown separately and in a plan view in FIG. 5. The lower surface of the support body 3 rises from its ring flange 3.0 with an inclined lectern or desk surface 3.2, on which the ULS vibrator 1 is fastened, as seen in FIG. 4. The ULS vibrator is in the form of a rectangular or square platelet and may be cemented in place. Approximately on the other half of the circular plan view, there is seen a grooved plateau surface 3.3 which drops steeply with a step surface 3.4 toward the ring flange 3.0 at the bottom. As seen in FIG. 5, ribs 3.5 which have a V or zig-zag-shaped cross section serve for scattering divergent ULS rays, which must not disturb a principal main beam.

The second beam probe housing G 2 (seen in particular in FIG. 3) is a rectangular prismatic body which has a central cylindrical opening 11 for the guiding surfaces 11.1 and the mounting surfaces 11.3, seen in FIG. 4.

The corner regions of the second housing G 2 which are designated with reference symbols E 1 to E 4, have at least two through holes B 1 and B 2 formed therein with upward-protruding tube connections (or nozzles) R 1 and R 2 for connecting non-illustrated coupling liquid feed lines. In particular, the second beam probe housing G 2 has a square shape as seen in the plan view of FIG. 3. Such a shape has point symmetry, i.e. it is particularly advantageous if adapted to the circular shape of the subarrangement PK 1, as seen in a plan view, particularly because all of the corner regions E 1 to E 4 are mutually equivalent.

It is particularly advantageous if the mounting holes B 1, B 2 and the nozzles R 1, R 2 inserted therein are diagonally opposite each other. In the illustrated example of FIG. 3, the holes and nozzles are disposed within the corner regions E 2, E 4. The corner E 1 has a tapped blind hole 13 for a clamping screw 14 of a hold-down spring 15. The hole 13 is not visible in detail from FIGS. 3 and 4 but can be seen in FIG. 10. The spring is constructed in the form of a forwardly curved leaf spring with a thickness of about 1 mm. A spherical part 15.1 of the free end of the spring 15 engages centrally at the upper surface of the beam probe subarrangement PK 1 and specifically, at an upper lid 16 of the subarrangement. The spring 15 has a hole formed in the other end thereof, so that it can be mounted on the shank of the clamping screw 14. In order to clamp the spring 15, a washer 17 is also inserted between the head of the clamping screw 14 and the leaf spring 15, and on the otherside of the leaf spring 15, a spacer bushing 18 holds the leaf spring 15 at a predetermined distance from the cover surface g 2.2 of the second housing G 2, as seen in FIG. 4. The clamping screw 14 is thus anchored in vicinity of a corner of the second housing G 2 which is free of through holes for coupling liquid.

The reference axis h of the beam probe PK or the subarrangement or subassembly PK 1 is intersected at a right angle by a joint axis k for a gimbal support of a beam probe. In the gimbal support, two joint pins Z 1 and Z 2 are disposed opposite each other on opposite sides of the second housing G 2. As shown in FIGS. 10 and 11, the joint pins are formed of a bevelled post 19, a stop shoulder 20 and a threaded shaft 21 for screwing into corresponding tapped holes 22.

Figure 16:
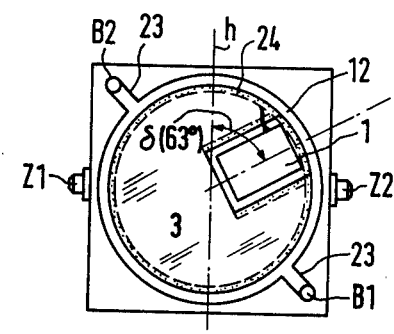
FIG. 16 is a bottom view of the device according to FIG. 8, although with the beam probe subarrangement inserted and an oblique angle changed from δ=46.5° to δ=63°.

As is shown in FIG. 11 in conjunction with FIG. 16, the opening of the through holes B 1 and B 2 are in communication with the annular gap 12 on the bottom for the coupling liquid, through substantially radial connecting canals 23.

FIG. 16 as well as FIG. 4 also show a cylindrical cork wall 24 which surrounds the support body 3 and the damping mass 4 and serves as an intermediate layer for the wall of the first housing G 1. Toward the top, the base body 10 of the housing G 1 is closed by the above-mentioned cover 16 which fits accurately into an annular setback 10.4 at the upper end of the base body 10, with a stepwise offset edge 16.1. Before the cover 16 is inserted, non-illustrated switching elements of a coil and a balancing resistor are connected to the ULS vibrator, and a solder joint for two connecting bushings A 1, A 2 is established. The cavities in the interior of the base body 10 which are not filled with the damping mass can then be provided with an epoxy resin, and the lid 16 is then put in place and joined and secured by means of the epoxy resin, forming a seal. The ring flange 3.0 of the support body on the bottom has a slight projecting length a 4 as compared to the inner diameter of the base body 10, so that a defined stop is provided when the support body is inserted through the opening 10.1.

The completed subarrangement PK 1 can then be inserted from above into the guiding and mounting surfaces 11.1, 11.3 of the second housing G 2. The structure is constructed in such a way that the mounting surfaces 11.3 of the second housing G 2 are disposed at a circular inner shoulder or circular collar and are spaced by an axial distance a 1 from the sliding bottom surfaces 11.2 or the surface 6.0 of the test piece. The sum of the circular shoulder height a 2 (see in FIG. 4) of the base body 10 and the thickness a 3 of the support body base 3.0, which protrudes from the base body 10 and has the coupling surface, is equal to the above-mentioned axial distance a 1, so that a flush termination of the sliding body surfaces 11.2 with the coupling surface 3.1 is obtained, except for the annular gap 12 for the coupling liquid. The entire coupling surface 3.1 can be wetted with a thin water film emerging from the annular gap 12.

As can be seen from FIG. 4, the subarrangement or subassembly PK 1 is only surrounded by the second beam probe housing G 2 over part of its height, so that at least one connecting jack or bushing A 1 or A 2 for the ULS vibrator 1 can be fastened above the second housing G 2 in the wall of an overhanging free cylindrical surface area 10.5 of the base body 10. As seen in FIG. 3, it is particularly advantageous if at least two parallel-connected jacks A 1, A 2 are fastened to the periphery of the base body at two different points. This is done in such a manner that if one jack A 1 or A 2 is covered up due to the oblique angle, the other jack A 2 or A 1, respectively, is still accessible. FIGS. 6 and 7 show a sector angle of 120° between two radially-oriented axes aa 1, aa 2 of the jacks A 1, A 2. FIG. 6 also shows radially-oriented drillholes 25 for the jacks. This is done because one of the jacks may fall in the region of the circumferential angle of the clamping screws 14 or one of the pipe stubs or connections R 1, R 2, depending on the size of the oblique angle $\delta$. Since the pitch of the pipe stubs R 1, R 2 and the blind tapped hole 13 for the clamping screw 14 is always 90° or $\frac{1}{4}$ of the circumference, the other jack always remains free for connection purposes if one jack is covered up. This is because the free jack or connecting bushing forms a circumferential angle of 120° relative to the first jack. The clamping screw 14 is preferably a cap screw with cylindrical head, as shown; it is likewise advantageous to provide a securing pin D in the form of a cap screw, as seen in FIGS. 3 and 4, through which the rotational angular position of the subarrangement PK 1 is fixed within the second housing C 2, for defining the oblique angle $\delta$.

The accurate adjustment and fixation of the oblique angle $\delta$ is of substantial importance. As shown in FIGS. 6 and 7, the disc-shaped support body base 3.0 has a marking d 1 at the periphery thereof, which is made, for instance, in the form of a notch. The notch serves for marking the reference axis h or the position $\delta=0$. The base body 10 carries a corresponding countermarking d 2 at the lower peripheral region thereof, which is likewise in the form of a notch or a scale marking. In the assembled condition of the subarrangement PK 1, the marking d 1 and the countermarking d 2 must be brought into coincidence, as shown in FIG. 6. At exactly the same point of the periphery as is occupied by the countermarking d 2, the outer surface of the base body 10 has a radial tapped hole 10.6, and the shell surfaces are provided on the outside with a counter bore 10.7. The securing pin in the form of the cap screw D (FIGS. 3 and 4), is screwed into this tapped hole 10.6, in such a way that the cylindrical head of the cap screw D rests with its lower surface against the counter bore 10.7. A number of second beam probe housings G 2 are currently being manufactured which are completely identical in principle but are provided at different points along their periphery with a cut C, that starts at a point along the guiding surfaces 11.1 corresponding to the desired size of the oblique angle, extends radially and is formed in such a way that the cylindrical head of the cap screw D fits accurately, i.e. without play as far as possible, into the cut. In FIG. 3, such a cut C 1 for the oblique angle $\delta 1=0$ and a cut C 2 for the above-mentioned oblique angle $\delta 2=-45°$, are shown. For manufacturing reasons it is advantageous if the cuts which are generally designated with reference symbol C, are made continuous.

In comparison with FIGS. 3 to 7, FIGS. 8 and 9 show a second beam probe housing G 2 which is provided for receiving a subarrangement or subassembly PK 1 with an oblique angle δ3=46.5°; the cut is designated with reference symbol C 3 and is located almost exactly in one of the corners. It can furthermore be seen that the diagonals for the leaf spring 15 and the pipe stubs R 1, R 2 are interchanged because the corner region E 4 is already occupied by the cut C 3 and is no longer available for a hole B 2.

FIG. 9 shows once more the overall structure of the second housing G 2 without the subarrangement PK 1 and its parts.

In the variation according to FIGS. 10 and 11, the cut C 4 is disposed inside the second housing G 2 in such a manner that an oblique angle of δ4=74.5° is formed, if a subarrangement is inserted into the second housing G 2. The diagonals for the pipe stubs R 1, R 2 or the through holes B 1, B 2 are placed as in FIG. 8. As is diagrammatically shown in the broken-away portion of FIG. 10, the second beam probe housing G 2 can be provided at its guiding surfaces with a counter gear pitch 26, through which a gear pitch on the outer periphery of the base body 10 can be made to engage with a multiplicity of relative angle positions, the number of relative positions being determined by the number of teeth or the fineness of the gear pitch. For instance, the oblique angle could be changeable and securable in angular steps of 5°, corresponding to such a gear pitch. In case of such a gear pitch, a fixation pin or the corresponding cap screw D would be unnecessary. The anti-rotation device is obtained by the gear pitch. However, even without a separate anti-rotation device, be it in the form of the counter-gear pitch 26 and the non-illustrated gear pitch or without the anti-rotation device formed of the cut C and the fixation pin D as shown, the elastic pressure forces which are exerted by the tensioned leaf spring in the direction of the axis of the beam probe PK are sufficient to prevent an undesired rotation or change of the oblique angle. The anti-rotation devices are nevertheless necessary for safety reasons because unintended loosening of the clamping screw 14 can never be precluded entirely and because disassembly and reassembly of the subarrangement from the second housing must be ensured without having to adjust the oblique angle anew.

Figure 12:
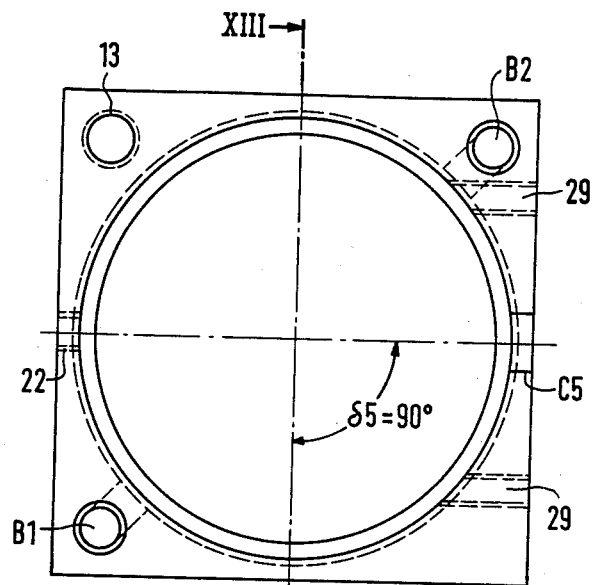
FIG. 12 is a top view of a fourth variant within the second embodiment with an oblique angle δ=90° and means for fastening a bearing journal plate.
Figure 13:
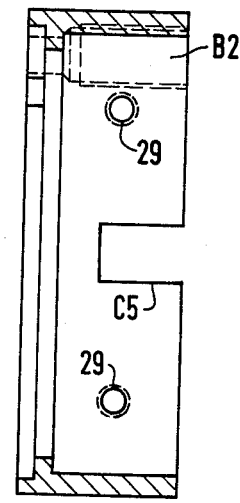
FIG. 13 is a cross-sectional view taken along the line XIII—XIII in FIG. 12, in the direction of the arrows.
Figure 15:
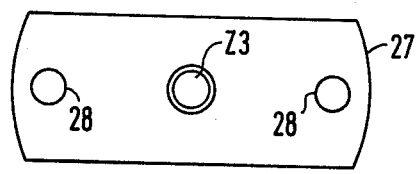
FIGS. 14 and 15 are respective side-elevational and top views of a bearing journal plate which is used if the position of the normal bearing journal is occupied by a marking slot in the case of a 90° oblique angle.
Figure 14:

FIGS. 12 to 14 also show a variation of the beam probe, in which the cut C 3 defines an oblique angle δ5 of 90°. Since this cut C 5 is accurately located in the peripheral region of a tapped hole for a joint pin Z 1 or Z 2, a separate joint plate 27 is provided according to FIGS. 13 to 15. The joint plate 27 has a central post Z 3 which has the same shape as the other posts Z 1, Z 2 and in addition has a mounting hole 28 at each of the ends thereof, through which the plate 27 can be bolted laterally by means of suitable non-illustrated fastening screws, to the side wall of the second housing C 2 having the cut C 5. For this purpose, suitable tapped holes 29 are provided in the second housing G 2.

It should be particularly emphasized that the guide and stop of the subarrangement or subassembly PK 1 within the second housing G 2 are simple and very accurate. The oblique angle adjustment made possible through the engagement of the fixation post and the cut can be made without force, i.e., fastening elements are not used. In this way, the adjustment accuracy is preserved even for frequent changes of the subarrangement PK 1. Any desired squint angle can be provided. For a laboratory-type or experimental setup, the oblique angle fixation by means of a fixation pin can be dispensed with in some circumstances. All of the parts in the subarrangement PK 1 and the second housing C 2 are identical except for the wedge angle of the support body, through which the incidence angle is determined and except for the arrangement of the cut C in the second housing, in which in special cases, a joint or bearing plate 27 must be used. The water connections are simple because the pipe stubs B 1 and B 2 are not set at an angle. The water channel at the bottom of the beam probe or at the beam probe bottom is generated by insertion of the subarrangement into the second housing G 2. This water channel or annular gap for the coupling liquid can therefore be cleaned easily. Shielding of the ULS vibrator and the associated switching elements and lines without a gap, is ensured by the terminating cover 16. The point of the sound outlet of the overall beam probe always remains intact when the subarrangement PK 1 is rotated for adjusting different oblique angles, since it is disposed at the center of rotation. The leaf spring mounting could also be referred to as a clamping bracket fastening; since it ensures a proper holding of the subarrangement even in the case of vibrations, without undesired forces being exerted onto the interior of the subarrangement.

We claim:

1. Special angle beam probe for ultrasonic testing of a test piece, comprising a multiplicity of prefabricated beam probe subassemblies disposed on a surface of the test piece, said beam probe subassemblies each having a first housing, a wedge-shaped support body disposed in said first housing, at least one ultrasonic vibrator fastened to said support body, and damping means disposed in said first housing, and a multiplicity of second beam probe housings each surrounding a respective one of said beam probe subassemblies, said vibrators each delivering an ultrasonic beam striking a given point along the surface of the test piece at the same predetermined incidence angle other than 0° as measured from a perpendicular to the surface of the test piece at the given point, said beams arriving at the surface of the test piece at oblique angles between 0° and 360° subtended between a principal axis of the beam probe and said beam, as seen in direction perpendical to the beam probe from above, means for fastening said beam probe subassemblies at least at one different predetermined oblique angle in said second beam probe housings, and means for assembling said second beam probe housings with said beam probe subassemblies having the same incidence angle and different oblique angles with different oblique angle relationships.

2. Special angle beam probe according to claim 1, wherein said first beam probe housings have a cylindrical base body having an opening formed in the bottom thereof and having annular shoulder surfaces at the front thereof, said support bodies have coupling surfaces protruding through said openings in said base bodies, and said second beam probe housings have cylindrical guiding surfaces, bottom sliding surfaces and mounting surfaces spaced from said bottom sliding surfaces in axial direction of the beam probe, said cylindrical base bodies of said beam probe subassemblies having the outer periphery thereof inserted and locked in said cylindrical guiding surfaces of said second beam probe housings, setting said predetermined oblique angle by rotation thereof, said annular shoulder surfaces being in engagement with said mounting surfaces defining annular gaps at the bottom of the beam probe for coupling liquid.

3. Special angle beam probe according to claim 2, wherein said second beam probe housings are substantially prismatic rectangular bodies each having a central opening formed therein defining said guiding and mounting surfaces, and said second beam probe housings have corner regions having at least two holes formed therethrough and upwardly-protruding pipe stubs integral therewith for connecting coupling liquid feedlines.

4. Special angle beam probe according to claim 3, wherein said second beam probe housings are square, as seen from above.

5. Special angle beam probe according to claim 3, wherein said pipe stubs are diagonally opposite each other.

6. Special angle beam probe according to claim 3, including at least one hold-down spring and a clamping screw anchored in a blind tapped hole formed in vicinity of a corner of said second beam probe housing which is free of said holes, said clamping screw tensioning said hold-down spring against the top of said beam probe subassemblies in each of said second beam probe housings, pushing said beam probe subassemblies against said mounting surfaces.

7. Special angle beam probe according to claim 6, wherein said clamping screw of each of said second beam probe housings has a shank, and said spring is a curved leaf spring having a hole formed therein through which said shank passes and a free end, said free end having a spherical part centrally disposed on the top of said beam probe subassembly.

8. Special angle beam probe according to claim 7, including a spacer bushing mounted on said shank above the top of said base body.

9. Special angle beam probe according to claim 3, wherein said second beam probe housing has substantially radial connecting canals formed therein connecting said holes to said annular gap.

10. Special angle beam probe according to claim 2, wherein said annular shoulder surfaces of said cylindrical base bodies are formed on an annular shoulder, said coupling surfaces of said support bodies are formed on bases thereof, said mounting surfaces of said second beam probe housings are formed on a circular inner shoulder and are disposed at a given axial distance from said bottom sliding surfaces and the surface of the test piece, and the sum of the height of said annular shoulder and the thickness of said support body base protruding from said base body for each beam probe subassembly is substantially equal to said given axial distance, whereby said bottom sliding surfaces and coupling surfaces are flush.

11. Special angle beam probe according to claim 2, including a lid liquid-tightly enclosing and shielding the top of said base body.

12. Special angle beam probe according to claim 11, including a lid liquid-tightly enclosing and shielding the top of said base body, at least one hold-down spring and a clamping screw anchored in a blind tapped hole formed in vicinity of a corner of said second beam probe housing which is free of said holes, said clamping screw tensioning said hold-down spring against said lid of said beam probe subassemblies in each of said second beam probe housings, pushing said beam probe subassemblies against said mounting surfaces.

13. Special angle beam probe according to claim 12, wherein said clamping screw of each of said second beam probe housings has a shank, and said spring is a curved leaf spring having a hole formed therein through which said shank passes and a free end, said free end having a spherical part centrally disposed on said lid of said beam probe subassembly.

14. Special angle beam probe according to claim 13, including a spacer bushing mounted on said shank above said lid of said base body.

15. Special angle beam probe according to claim 2, wherein said second beam probe housings only surround part of the height of said beam probe subassemblies, defining protruding free shell regions of said base body, and including at least one connector jack connected to said vibrators and fastened to said free shell regions.

16. Special angle beam probe according to claim 15, wherein said at least one connector jack is in the form of at least two parallel-connected connector jacks fastened to two different points of the periphery of each of said base bodies, whereby one of said jacks is always accessible if the other is covered up due to said squint angle.

17. Special angle beam probe according to claim 16, wherein the axes of said jacks are radially oriented and form a sector angle of substantially 120°.

18. Special angle beam probe according to claim 2, wherein said coupling surfaces of said support bodies are formed on bases thereof, and including a first marking on the periphery of each of said bases defining a beam probe reference axes where said oblique angle=0°, and said base bodies having a lower peripheral region having a second corresponding counter marking coinciding with said first marking in assembled condition of said beam probe subassemblies.

19. Special angle beam probe according to claim 18, wherein said bases of said support bodies are circular discs and said markings are notches.

20. Special angle beam probe according to claim 18, wherein at the point along the periphery of said base bodies having said second markings, said base bodies have radially-oriented posts and said second beam probe housings have radially-extended cuts formed therein receiving said posts, said cuts extending from a point on said guiding surfaces corresponding to the desired oblique angle and said cuts being matched to the dimensions of said posts for fixing said oblique angle without play.

21. Special angle beam probe according to claim 2, wherein said base body has a gear pitch formed on the outer periphery thereof and said second beam probe housing has a counter gear pitch at said guiding surfaces matching said gear pitch, for changing and securing said oblique angle in accordance with the tooth pitch by rotating said beam probe subassembly relative to said second beam probe housing in angular steps.

22. Special angle beam probe according to claim 1, including bearing posts for a gimbal support of a beam probe mounting disposed along another principal axis of said beam probe housing crossing said first-mentioned principal beam probe axis at a right angle on two opposite side walls of said second beam probe housing.

23. Special angle beam probe according to claim 22, wherein said base body has a gear pitch formed on the outer periphery thereof and said second beam probe housing has a counter gear pitch at said guiding surfaces matching said gear pitch, for changing and securing said oblique angle in accordance with the tooth pitch by rotating said beam probe subassembly relative to said second beam probe housing in angular steps.

24. Special angle beam probe according to claim 1, wherein said support body is formed of a material from the group consisting of resinous and plastic material.

25. Special angle beam probe for ultrasonic testing of a test piece, comprising a prefabricated beam probe subassembly disposed on a surface of the test piece, said beam probe subassembly having a first housing, a wedge-shaped support body disposed in said first housing, at least one ultrasonic vibrator fastened to said support body, and damping means disposed in said first housing, and a second beam probe housing surrounding said beam probe subassembly, said vibrator delivering an ultrasonic beam striking a given point along the surface of the test piece at a predetermined incidence angle other than 0° as measured from a perpendicular to the surface of the test piece at the given point, said beam arriving at the surface of the test piece at an oblique angle between 0° and 360° subtended between a principal axis of the beam probe and said beam, as seen in direction perpendicular to the beam probe from above, means for fastening said beam probe subassembly at least at one predetermined oblique angle in said second beam probe housing.

* * * * *